(12) United States Patent
McGarity et al.

(10) Patent No.: US 8,152,834 B2
(45) Date of Patent: Apr. 10, 2012

(54) FORCEPS AND SYSTEM USING SAME

(75) Inventors: Owen Carlos McGarity, Swarthmore, PA (US); Bryan Griffiths, Coatesville, PA (US)

(73) Assignee: Synthes USA, LLC, West Chester, PA (US)

( * ) Notice: Subject to any disclaimer, the term of this patent is extended or adjusted under 35 U.S.C. 154(b) by 451 days.

(21) Appl. No.: 11/105,661

(22) Filed: Apr. 13, 2005

(65) Prior Publication Data

US 2006/0235466 A1    Oct. 19, 2006

(51) Int. Cl.
*A61B 17/00*    (2006.01)

(52) U.S. Cl. ............................................. 606/205

(58) Field of Classification Search ............. 606/151, 606/157, 174, 205–208, 210–211; 433/3, 433/4, 7, 13, 159, 160; 81/416; D24/133, D24/143
See application file for complete search history.

(56) References Cited

U.S. PATENT DOCUMENTS

| | | | |
|---|---|---|---|
| 254,643 A | 3/1882 | Hamilton | 7/100 |
| 256,525 A | 4/1882 | Whiting | 24/31 R |
| 360,695 A | 4/1887 | Holmes | |
| 455,822 A | 7/1891 | Weber | 7/127 |
| 597,582 A | 1/1898 | Knapp | |
| 620,853 A * | 3/1899 | Richter | 606/208 |
| 827,392 A | 7/1906 | Prangemeier | 81/426.5 |
| 864,558 A | 8/1907 | Richter | 606/208 |
| 891,061 A | 6/1908 | Hansen | 81/302 |
| 1,001,042 A | 8/1911 | Kadel | 411/433 |
| 1,021,110 A | 3/1912 | Niewohner | 411/244 |
| 1,333,243 A | 3/1920 | Bowers | 81/424.5 |
| 1,973,569 A | 9/1934 | Kurtz | 606/208 |
| 2,375,094 A * | 5/1945 | Flanagan | 433/4 |
| 2,387,928 A | 10/1945 | Monnier | 81/426.5 |
| 2,632,661 A * | 3/1953 | Cristofv | 403/119 |
| 2,641,149 A | 6/1953 | Petersen | 81/380 |
| 2,932,894 A * | 4/1960 | Sheldon | 433/4 |
| 3,161,085 A | 12/1964 | Pratt | 81/3.8 |
| 3,202,023 A | 8/1965 | Parker | 81/421 |
| 3,329,001 A | 7/1967 | Ringzelli et al. | 72/409.17 |
| 3,454,001 A | 7/1969 | Stockfisch | |
| 3,473,528 A | 10/1969 | Mishkin et al. | |
| 3,653,284 A | 4/1972 | Pynchon et al. | 81/426.5 |
| 4,035,917 A * | 7/1977 | Roberts | 433/145 |
| 4,144,643 A | 3/1979 | Krygier | |
| 4,179,782 A | 12/1979 | Forman et al. | 29/268 |

(Continued)

FOREIGN PATENT DOCUMENTS

AT    192049    9/1957

(Continued)

OTHER PUBLICATIONS

English Abstract of WO 96/28110 dated Sep. 19, 1996.

(Continued)

*Primary Examiner* — Corrine M McDermott
*Assistant Examiner* — Dianne Dornbusch
(74) *Attorney, Agent, or Firm* — Woodcock Washburn LLP

(57) ABSTRACT

A pair of forceps including first and second elongated members pivotally connected together. A handle and a head are defined at opposing ends of the first and second elongated members. In one preferred embodiment, a threaded cannula receiving chamber is disposed in the head, and the elongated members are separable via manipulation of the first and second elongated members with respect to each other.

26 Claims, 4 Drawing Sheets

U.S. PATENT DOCUMENTS

| | | | |
|---|---|---|---|
| 4,308,863 A | 1/1982 | Fischer | |
| 4,318,316 A | 3/1982 | Guilliams | 81/426.5 |
| 4,353,273 A | 10/1982 | Freberg | 81/424.5 |
| 4,361,130 A | 11/1982 | Maglia | 125/36 |
| 4,386,603 A | 6/1983 | Mayfield | |
| 4,445,513 A | 5/1984 | Ulrich et al. | |
| 4,730,608 A | 3/1988 | Schlein | |
| 4,848,368 A | 7/1989 | Kronner | |
| 5,023,989 A | 6/1991 | Hargrave | 29/426.5 |
| D323,214 S * | 1/1992 | Carchidi | D24/143 |
| 5,084,935 A * | 2/1992 | Kalthoff | 7/132 |
| 5,120,221 A * | 6/1992 | Orenstein et al. | 433/159 |
| 5,147,358 A | 9/1992 | Remmler | |
| 5,197,879 A * | 3/1993 | Fowler et al. | 433/159 |
| 5,232,360 A * | 8/1993 | Ingels | 433/4 |
| 5,391,181 A | 2/1995 | Johnson et al. | 606/207 |
| 5,562,447 A * | 10/1996 | Moy et al. | 433/150 |
| 5,564,920 A | 10/1996 | Klapper et al. | |
| 5,575,790 A | 11/1996 | Chen et al. | |
| 5,624,454 A | 4/1997 | Palti et al. | 606/151 |
| 5,746,757 A * | 5/1998 | McGuire | 606/148 |
| 5,769,850 A | 6/1998 | Chin | |
| 5,799,381 A | 9/1998 | Gannon et al. | 29/268 |
| 5,829,323 A | 11/1998 | Liston | 81/44 |
| 5,885,283 A | 3/1999 | Gittleman | |
| 5,885,290 A | 3/1999 | Guerrero et al. | |
| 5,891,161 A * | 4/1999 | Graser | 606/148 |
| 5,902,304 A | 5/1999 | Walker et al. | |
| 5,993,448 A | 11/1999 | Remmler | |
| 6,036,692 A | 3/2000 | Burel et al. | 606/61 |
| 6,051,004 A | 4/2000 | Gill | 606/147 |
| 6,206,882 B1 | 3/2001 | Cohen | |
| 6,256,855 B1 | 7/2001 | Schall | 29/275 |
| 6,267,589 B1 | 7/2001 | Farzin-Nia et al. | |
| 6,328,745 B1 | 12/2001 | Ascherman | |
| 6,361,541 B1 | 3/2002 | Barnhart | 606/108 |
| 6,413,088 B1 | 7/2002 | Kawaguchi | |
| 6,428,544 B1 * | 8/2002 | Ralph et al. | 606/99 |
| 7,165,970 B2 * | 1/2007 | Anderson | 433/159 |
| 7,318,725 B2 * | 1/2008 | Zepf | 433/159 |
| 7,588,579 B2 | 9/2009 | Mommaerts | |
| 2001/0004858 A1 | 6/2001 | Kachergius | 81/424.5 |
| 2002/0031741 A1 | 3/2002 | Williams | |
| 2004/0093020 A1 * | 5/2004 | Sinton | 606/208 |
| 2004/0106947 A1 | 6/2004 | Propp et al. | 606/208 |
| 2004/0152044 A1 * | 8/2004 | Khan-Sullman | 433/159 |
| 2005/0004590 A1 | 1/2005 | Waters et al. | 606/170 |
| 2005/0033339 A1 * | 2/2005 | Grayzel et al. | 606/174 |
| 2005/0186536 A1 * | 8/2005 | Zepf | 433/159 |
| 2005/0191598 A1 * | 9/2005 | Anderson | 433/159 |

FOREIGN PATENT DOCUMENTS

| | | |
|---|---|---|
| DE | 743 853 C | 1/1944 |
| DE | 1049533 | 1/1959 |
| DE | 41 15 548 A1 | 11/1991 |
| DE | 202004002560 U1 | 4/2004 |
| EP | 0706349 B1 | 8/1999 |
| EP | 0846446 B1 | 8/2003 |
| JP | 2001-340354 | 12/2001 |
| WO | WO 96/28110 A2 | 9/1996 |
| WO | WO 96/29964 A1 | 10/1996 |
| WO | WO 98/10708 A1 | 3/1998 |

OTHER PUBLICATIONS

English Abstract of WO 98/10708 dated Mar. 19, 1998.

Mommaerts, M.Y., "Transpalatal distraction as a method of maxillary expansion," British Journal of Oral and Maxillofacial Surgery, 1999, 37, pp. 268-272.

"Malleable". Merriam-Webster Dictionary [online], [retrieved on Nov. 9, 2006], Retrieved from the internet <URL: www.m-w.com.

"Thread". Merriam-Webster Dictionary [online], [retrieved on Nov. 9, 2006], Retrieved from the internet <URL: www.m-w.com .

* cited by examiner

FORCEPS AND SYSTEM USING SAME

FIELD OF THE INVENTION

The present invention relates to forceps, and systems and methods employing the same. Among the many different and non-limiting applications, the forceps are useful for both gripping a cannula that is inserted through soft tissue and retracting the surrounding soft tissue.

BACKGROUND OF THE INVENTION

One technique for stabilizing a fractured mandible includes attaching a plate to the mandible. A small incision is made in the patient's cheek, and a cannula is inserted through the incision. A plate is passed through the patient's mouth and positioned in an area proximate the fracture. A drill bit can be fed through the cannula for drilling pilot holes into the mandible. Fasteners and fastening devices can also be fed through the cannula to secure the plate to the patient's mandible. Some maxillofacial techniques only use wire, screws or pins, and not a plate, for stabilizing fractured mandibles. A cannula is typically used to drill pilot holes and/or position and secure the wire, screws or pins appropriately.

Grasping forceps can be used to engage the inserted cannula so that it does not move during the drilling and/or fastening steps. As can be seen in FIG. 1, a head portion of a pair of forceps is placed into the patient's mouth to engage a section of the inserted cannula. The head portion and/or a handle portion may be angled in an upward direction to retract the patient's cheek. The retraction creates a line of sight and/or improves the field of vision for the medical attendant to observe the area where the hardware is being installed, and to ensure the well being of the patient.

An example of prior art forceps is shown in FIG. 2. Forceps 1 includes pivotally connected arms 2 and 3, a head region 4 and a handle region 5. Head region 4 comprises a chamber 6 for engaging a cannula or other device. Embodiments of the present invention offer substantial improvements over these and other prior art forceps.

SUMMARY OF THE INVENTION

In accordance with one preferred embodiment of the present invention, there has now been provided a pair of forceps having first and second elongated members pivotally connected. The first elongated member includes a first head portion and an opposing first handle portion that is angled in a first direction with respect to the first head portion. The first head portion has a first joint component and a tissue contacting surface facing the first direction. The second elongated member includes a second head portion and an opposing second handle portion. The second head portion employs a second joint component that is configured for engaging the first joint component. The first and second joint components are capable of assembly and disassembly without the use of tools. And the first and second joint components are spaced apart from the tissue contacting surface.

In accordance with another preferred embodiment, there has now been provided a pair of forceps having first and second elongated members pivotally and separably connected. A handle is defined at one end, and a head is defined at an opposing end. The head includes first and second jaws, each of which is associated with a respective one of the first and second elongated members and including an inner surface. A groove is formed in each of the inner surfaces to collectively define a substantially cylindrical gripping chamber upon converging the two jaws. A tissue retracting surface is defined by a surface of at least one of the head and the handle. The tissue retracting surface is oriented orthogonal to the inner surfaces and has a width of at least about 15 mm.

In accordance with yet another preferred embodiment, there has now been provided a pair of forceps having first and second elongated members pivotally connected. A handle is defined at one end, and a head is defined at an opposing end. A cannula receiving chamber is disposed in the head and has a threaded surface. The first and second elongated members are separable via manipulation of the first and second elongated members with respect to each other.

In accordance with another preferred embodiment, there has now been provided a pair of forceps including a head portion having a first jaw, and a second jaw pivotally connected to the first jaw. Each of the first jaw and the second jaw includes an inner surface having a proximal end and a distal end. The inner surfaces are tapered inwardly in a direction from the distal end to the proximal end to define an engagement guide capable of facilitating blind location and engagement of a cannula. A groove is formed in each of the inner surfaces to collectively define a cannula-receiving chamber upon converging said first and second jaws. The grooves are located at the respective proximal ends of the inner surfaces so that a cannula can be positively engaged by passing the first and second jaws around the cannula via the engagement guide until travel is inhibited (that is, the first and second jaws are bottomed out) and then converging the first and second jaws around the cannula.

These and various other features of novelty, and their respective advantages, are pointed out with particularity in the claims annexed hereto and forming a part hereof. However, for a better understanding of aspects of the invention, reference should be made to the drawings which form a further part hereof, and to the accompanying descriptive matter, in which there is illustrated preferred embodiments.

DETAILED DESCRIPTION OF ILLUSTRATIVE EMBODIMENTS

The present invention may be understood more readily by reference to the following detailed description of illustrative and preferred embodiments taken in connection with the accompanying figures that form a part of this disclosure. It is to be understood that the scope of the claims is not limited to the specific devices, methods, conditions or parameters described and/or shown herein, and that the terminology used herein is for the purpose of describing particular embodiments by way of example only and is not intended to be limiting of the claimed invention. Also, as used in the specification including the appended claims, the singular forms "a," "an," and "the" include the plural, and reference to a particular numerical value includes at least that particular value, unless the context clearly dictates otherwise. When a range of values is expressed, another embodiment includes from the one particular value and/or to the other particular value. Similarly, when values are expressed as approximations, by use of the antecedent "about," it will be understood that the particular value forms another embodiment. All ranges are inclusive and combinable.

Figure 1:
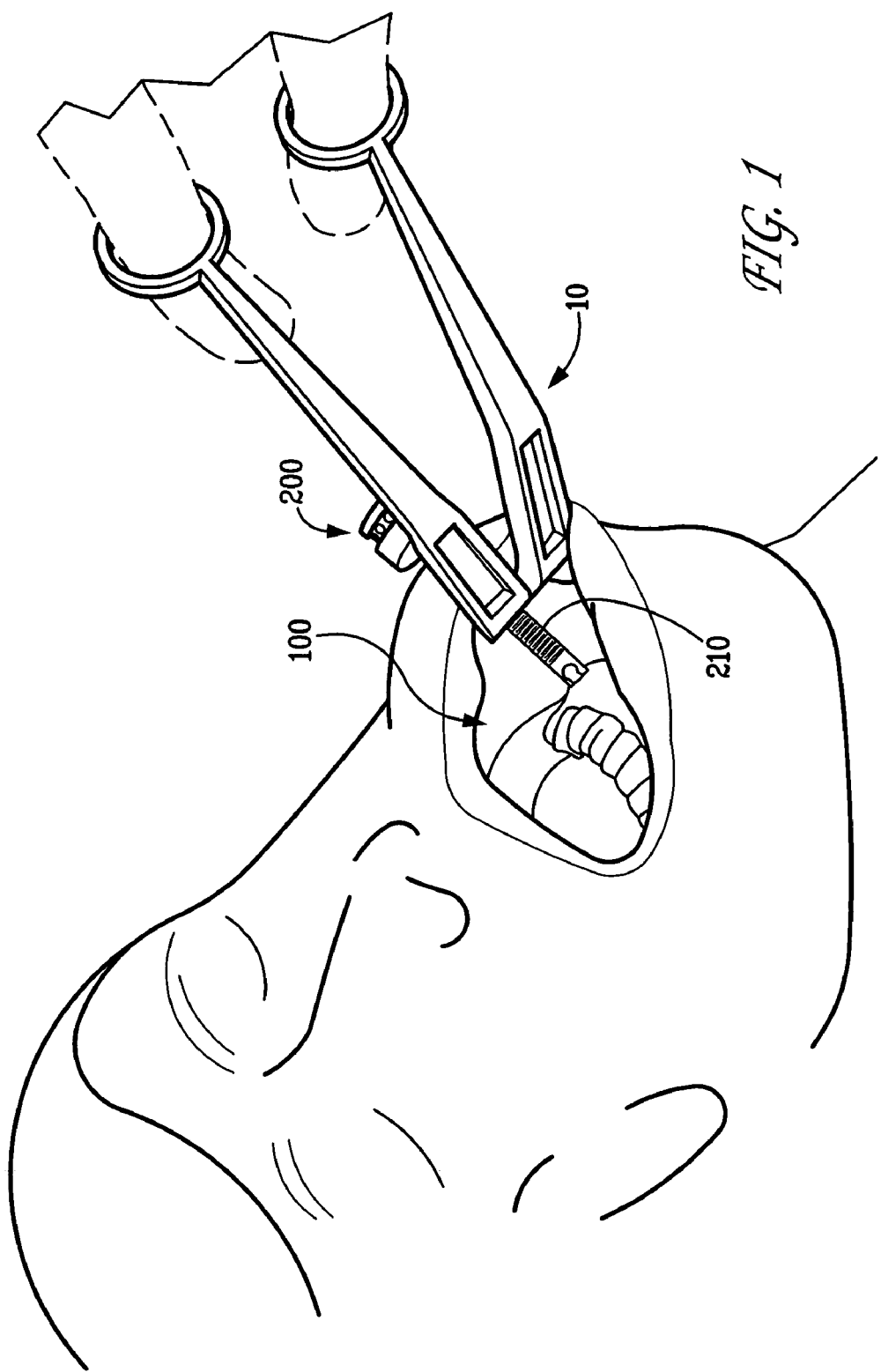
FIG. 1 is a perspective view of one preferred forceps embodiment being used in one preferred application.
Figure 2:
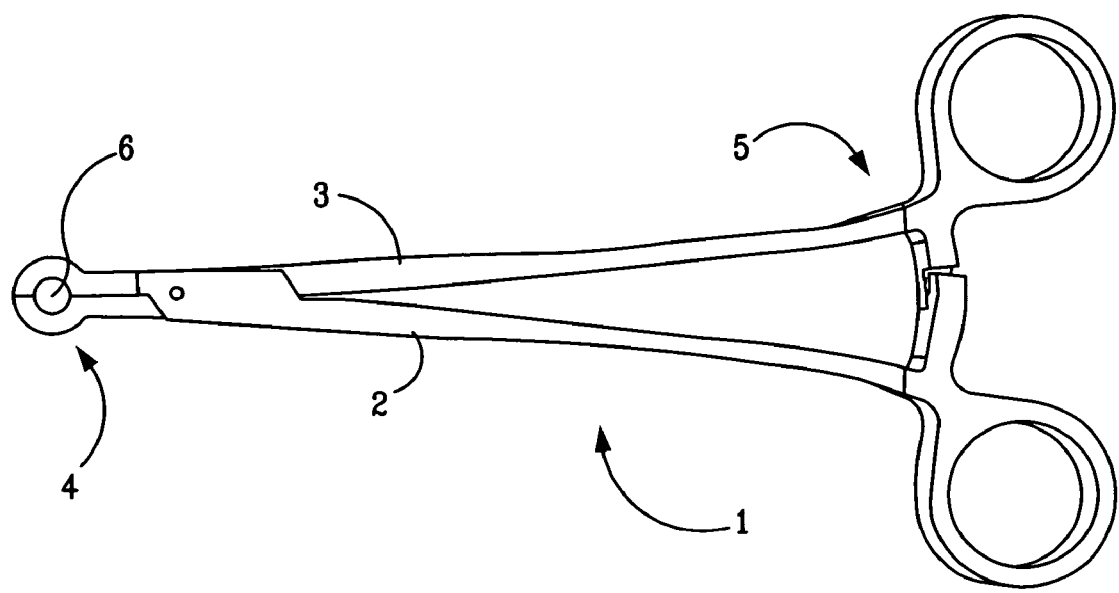
FIG. 2 is a top plan view of a prior art pair of forceps.

Referring now to the figures, wherein like features are labeled with like reference characters, an exemplary pair of forceps 10 is shown in FIG. 1 being used in one preferred application—a maxillofacial operation involving inserting self-drilling screws into a human mandible. Forceps 10 is shown inserted into the patient's mouth 100 and around a threaded cannula 200.

Figure 3:
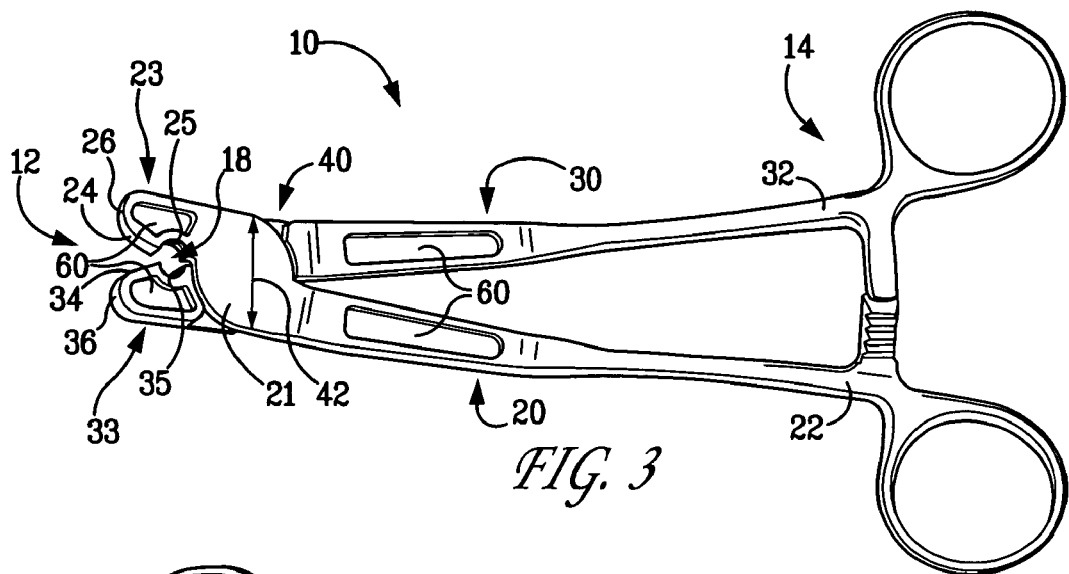
FIG. 3 is a top plan view of the preferred forceps shown in FIG. 1.
Figure 4:
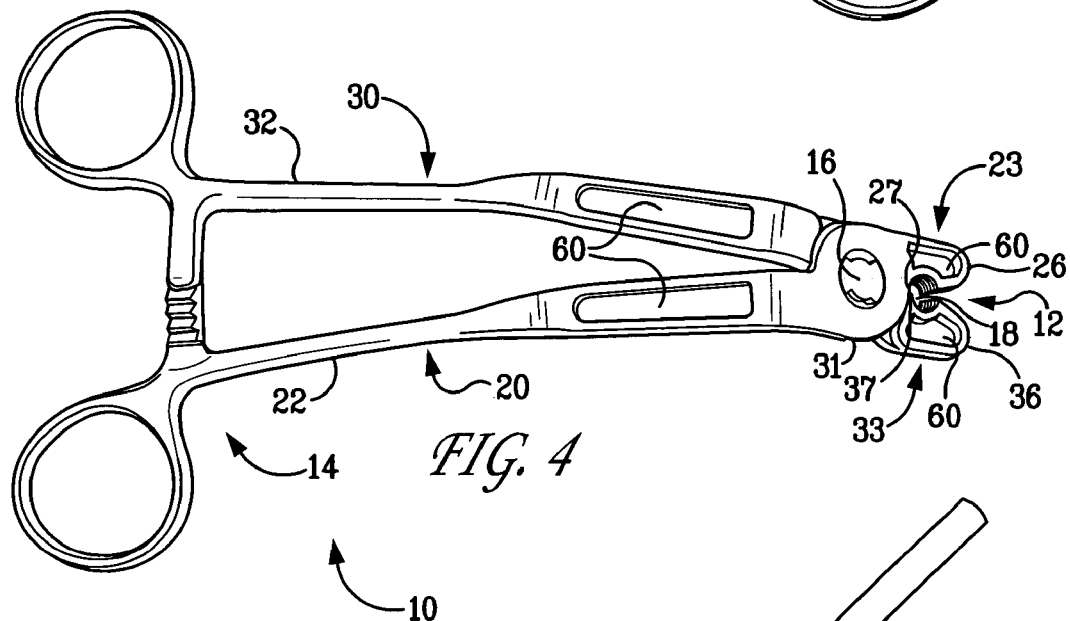
FIG. 4 is a bottom plan view of the preferred forceps shown in FIG. 1.
Figure 5:
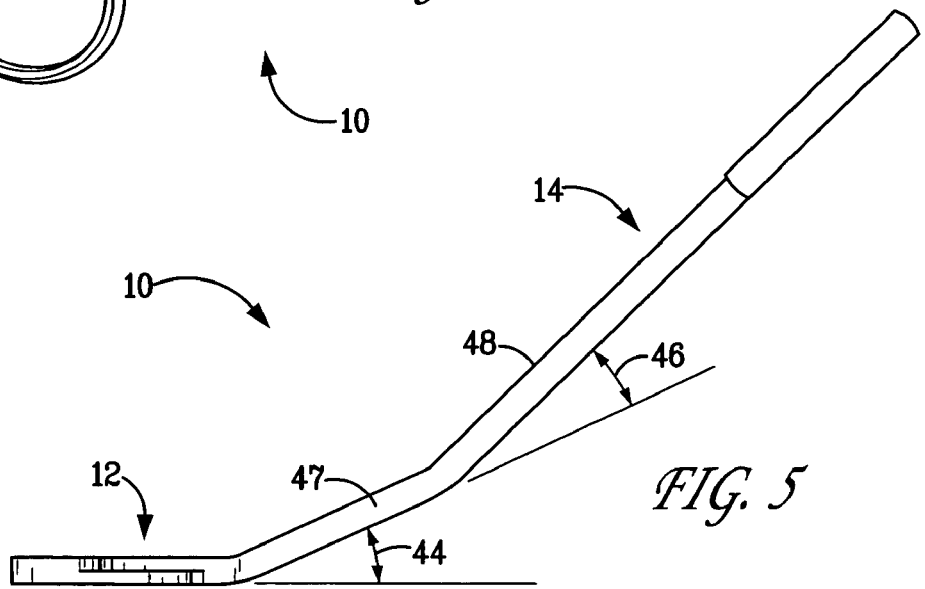
FIG. 5 is a side view of the preferred forceps shown in FIG. 1.

Referring now to FIGS. 3-5, exemplary forceps 10 includes first and second elongated members or arms 20 and 30 pivotally connected together. A head 12 is defined by respective head portions 21 and 31, and a handle 14 is defined by handle portions 22 and 32. Elongated members 20 and 30 are connected at a joint 16. In preferred embodiments, joint 16 is non-permanent; that is, the forceps are designed and manufactured to be disassembled for packaging, cleaning/sterilization, and assembled for use. Note that permanent joints can be used in alternative embodiments.

Each of head portions 21 and 31 includes a jaw 23, 33 having an inner surface 24, 34. The inner jaw surfaces comprise a groove 25, 35 that collectively define a gripping chamber 18 when jaws 23 and 33 are converged. Gripping chamber 18 preferably is threaded to facilitate a secure engagement of a cannula or other device. Non-threaded gripping chambers however can equally be employed. Gripping chamber is shown being substantially cylindrical, but it is not limited to this geometry. Outer surfaces of a cannula or any other device may also be threaded (see, for example, threads 210 on cannula 200 shown in FIG. 1), such that the threads associated with gripping chamber 18 can engage threads on the device or object being grasped.

As shown in FIGS. 3-5, inner jaw surfaces 24 and 34 are tapered outwardly in a direction from gripping chamber 18 to respective distal ends 26, 36 of the jaws to define an engagement guide ("V-entry"). Distal ends 26 and 36 are preferably rounded, or otherwise blunt, to prevent injury to the medical attendant or patient. In preferred embodiments, gripping chamber 18 is located at respective proximal ends 27, 37 of the jaws so that a cannula or other device can be positively engaged by "bottoming out" the jaws around a cannula. These "V-entry" and "bottoming out" features are optional, and can be employed to facilitate blind location and engagement of a device, particularly when the device is positioned in an area having a limited field of vision, such as, for example, in a patient's mouth.

In addition to grasping a cannula during a maxillofacial procedure, forceps 10 can also be used to retract soft tissue. This is shown in FIG. 1. The patient's cheek is retracted or pulled away from its normal resting position to enable a medical attendant to observe what is happening inside the mouth, and to permit placement and manipulation of objects into the mouth. At least some of the head and/or the handle generally define a tissue contacting surface. Soft tissue can generally be retracted through geometrical and/or dimensional aspects of the tissue contacting surface, by simply moving the forceps after contacting the soft tissue, or through a combination of the two.

Referring again to FIGS. 3-5, forceps 10 have a tissue contacting (retracting) surface 40 that is primarily defined by the outer surface of head portion 21, and partially defined by exposed portions of an outer surface of head portion 31. Depending on the length of the forceps' head and the depth of insertion into the mouth (or other area), tissue contacting surface 40 may also be partially defined by adjacent handle portions 22 and 32. Tissue contacting surface 40 has a width 42 that is preferably between about 5 and 50 mm, more preferably at least about 15 mm, and even more-preferably at least about 20 mm.

A side view of exemplary forceps 10 is shown in FIG. 5. From this view, one can see that handle 14 can be angled with respect to head 12 at an angle 44. Generally, angle 44 is between about 10 degrees and 90 degrees, preferably between about 10 degrees and 45 degrees, and more preferably between about 20 degrees and 30 degrees. In one preferred embodiment, angle 44 is around 25 degrees. Handle 14 may also be parallel with head 12; that is, angle 44 would be substantially 0 degrees. In preferred embodiments, and as shown in the figures, handle 14 is angled in a direction towards tissue contact surface 40. Handle 14 itself can also contain an angle 46 that is preferably on the order of about 10 degrees to about 30 degrees, and more preferably about 20 degrees, although smaller and larger angles are contemplated by the present invention. Angle 46 is defined at the intersection of linear handle sections 47 and 48. An elevation change from head 12 to a distal end of handle 14 can be accomplished as shown, through multiple linear sections and corresponding angles (similar or dissimilar in magnitude), through one or more curvilinear sections, through a combination of linear and curvilinear sections, or through other manners known to the skilled artisan.

Since a tissue contacting surface may be at least partially defined by the forceps' handle, an elevation change from the head to a distal end of the handle may facilitate the retracting function of the forceps. Further, and in preferred embodiments, handle section 47 (of each handle portion) has a rectangular cross-sectional shape and is oriented so as to maximize the width of the respective handle portions, which in turn, may facilitate the tissue retraction function. As shown, handle section 48 (of each handle portion) has a circular cross-sectional area. Other cross-sectional shapes can equally be employed. And the forceps' handle may have a homogenous or heterogeneous cross-sectional shape.

Head portions 21, 31 and handle portions 22, 32 may optionally comprise cavities 60 formed in various surfaces, including the top and bottom surfaces, as is shown in the figures. Cavities 60 allow preferred forceps embodiments to employ wide tissue contacting surfaces without substantially increasing the metal requirements for their manufacture. If cavities are employed, it should be understood that there are no limitations to the size, geometry, or uniformity of the cavities.

Figure 6:
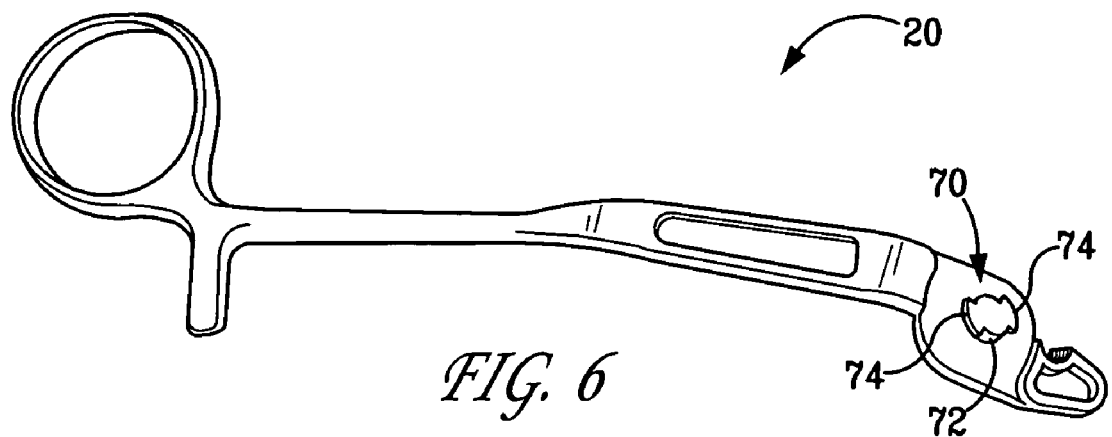
FIG. 6 is a perspective view of one of the elongated members of the preferred forceps shown in FIG. 1.

Elongated members 20 and 30 are preferably separable, with our without the use of tools. Referring now to FIG. 6, elongated member 20 is shown separated from elongated member 30. Elongated member 20 has a male joint component 70 extending from a surface of its head portion 21. Male joint component 70 includes a post 72 and a flange 74 disposed circumferentially around post 72, preferably in a non-continuous manner. The configuration of post 72 and flange 74 may differ from that shown in FIG. 6. Male joint component 70 may be integrally formed with elongated member 20, or may alternately be manufactured separately and then joined to member 20 with any number of techniques.

Figure 7:
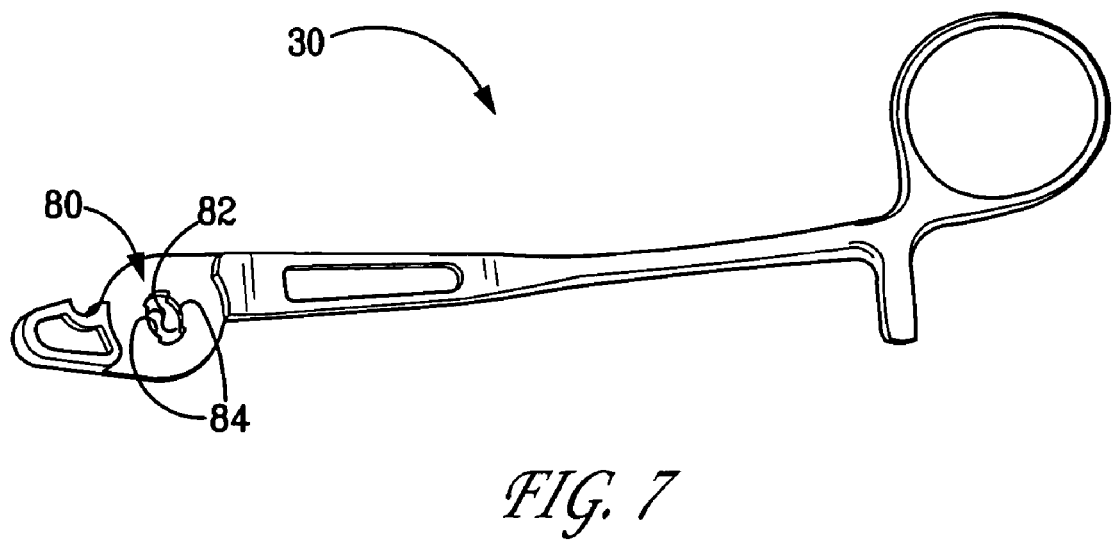
FIG. 7 is a perspective view of the other elongated member of the preferred forceps shown in FIG. 1.

Elongated member 30 is depicted in FIG. 7. Elongated member 30 has a female joint component 80 defined by an aperture 82 and a rib 84 disposed on the aperture's surface, preferably in a non-continuous manner. Female joint component 80 similarly may be integrally formed with elongated member 30 or separately manufactured. Aperture 82 may alternately take the form of a recess in head portion 31. To assemble elongated members 20 and 30, male and female joint members 70, 80 are first aligned so that flange 74 and rib 84 can slip past each other, the elongated members are converged and then rotated sufficiently to position rib 84 under flange 74. Asymmetric design of the elongated members and associated joint members, in preferred embodiments, prevents a user from assembling the forceps incorrectly. Elongated members 20 and 30 are simply rotated in an opposite direction and pulled apart for disassembly. One of ordinary skill in the art should readily appreciate that other types of joints and corresponding joint components can be used to effect the preferred separability aspect. And different types of manipulation and steps may be required for assembly and disassembly in comparison to that described above.

In accordance with the invention, preferred forceps embodiments may be used for retracting a patient's cheek and/or performing one or more maxillofacial procedures. For example, a method for retracting a patient's cheek is provided, comprising the steps of assembling exemplary elongated members 20 and 30 (preferably without the use of tools) and positioning the assembled forceps into a patient's mouth so that the patient's cheek is retracted from its normal resting position. Various maxillofacial procedures, such as, for example, stabilizing a fractured mandible, can be facilitated via the preferred retracting forceps. A cannula is typically inserted through a patient's cheek, during some maxillofacial procedures, to permit the passage of instruments and/or fasteners. The forceps can be inserted through the patient's mouth to securely hold the cannula, while also retracting the patient's cheek. After completing the procedure, the forceps can be disassembled for cleaning and/or sterilization. The forceps are preferably separable so that surfaces are non-contacting during sterilization to help ensure the sterilization is effective. The forceps can then be reassembled and employed for another chosen procedure.

Forceps in accordance with preferred embodiments can be made from any bio-inert material, for example, stainless steel or titanium. The forceps may optionally contain a coating or medicament. The forceps may be made through any number of manufacturing techniques known to the skilled artisan, including, but not limited to, forging and metal injection molding.

The preferred embodiments have been shown and described for grasping a cannula. It should be understood however, that forceps embodiments provided by the present invention may be used for grasping other devices, such as, for example, tubing, absorbent articles, and implantable members, as well as hard and soft tissue, or for any other grasping, cutting, or tearing. Further, while the present invention has been described in connection with the preferred embodiments of the various figures, it is to be understood that other similar embodiments may be used or modifications and additions may be made to the described embodiment for performing the same function of the present invention without deviating therefrom. Therefore, the present invention should not be limited to any single embodiment, but rather construed in breadth and scope in accordance with the recitation of the appended claims.

What is claimed:

1. A pair of forceps, comprising:
   (a) a first elongated member including a first head portion and an opposing first handle portion that is angled with respect to the first head portion, the first head portion comprising:
      (i) a first joint component;
      (ii) a tissue contacting surface configured to retract an area of soft tissue;
      (iii) a first recessed groove located distally from the first joint component; and
      (iv) a first inner jaw surface extending distally from the first recessed groove to a distal end of the first head portion;
   (b) a second elongated member pivotally connected to the first elongated member, the second elongated member including a second head portion and an opposing second handle portion; the second head portion including
      (i) a second joint component configured to engage the first joint component so as to pivotally couple the first and second elongated members;
      (ii) a second recessed groove located distally from the second joint component; and
      (iii) a second inner jaw surface extending distally from the second recessed groove to a distal end of the second head portion, such that the first and second inner jaw surfaces flare away from each other when the first and second joint components are assembled together and the forceps are in a fully closed configuration, wherein the first and second recessed grooves collectively define a substantially cylindrical gripping chamber with openings located at the tissue contacting surface and an outer surface opposite the tissue contacting surface.

2. The pair of forceps according to claim 1, wherein the tissue contacting surface is partially defined by portions of the second head portion that are exposed and that face the first direction.

3. The pair of forceps according to claim 1, wherein the tissue contacting surface includes a width of at least about 15 mm.

4. The pair of forceps according to claim 1, wherein the gripping chamber includes a threaded surface.

5. The pair of forceps according to claim 1, wherein the first handle portion is angled with respect to the first head portion at an angle between about 10 degrees and about 45 degrees.

6. The pair of forceps according to claim 5, where in the first handle portion is non-linear.

7. The pair of forceps according to claim 1, wherein the first joint component is a post extending from a surface of the first head portion that is opposite the tissue contacting surface, the post including a non-continuous flange disposed circumferentially around the post.

8. The pair of forceps according to claim 7, wherein the second joint component is an aperture extending through the second head portion, the aperture including a non-continuous rib disposed circumferentially around aperture wall.

9. The pair of forceps according to claim 1, wherein the first handle portion that is angled in a first direction with respect to the first head portion, and the tissue contacting surface faces the first direction.

10. The pair of forceps according to claim 1, wherein the first and second inner jaw surfaces are tapered outwardly away from each other at the distal ends of the respective first and second head portions.

11. The pair of forceps according to claim 1, wherein the first and second joint components are capable of assembly and disassembly by hand without the use of tools, and the first and second joint components are spaced apart from the tissue contacting surface so as not to irritate the soft tissue.

12. The pair of forceps according to claim 1, wherein the first and second inner surfaces define a V-shaped engagement guide to the recessed groove.

13. The pair of forceps according to claim 1, wherein the first and second inner jaw surfaces are flared away from each other from the gripping chamber to distal ends of the first and second head portions, respectively, when the forceps are in the fully closed configuration.

14. The pair of forceps according to claim 1, wherein the first and second inner jaw surfaces curve away from each other when the first and second joint components are assembled together and the forceps are in a fully closed configuration.

15. A pair of forceps, comprising:
  first and second elongated members pivotally connected together;
  a handle defined at one end of the first and second elongated members;
  a head defined at an opposing end of the first and second elongated members, the head having a distal end;
  a jaw within the head;
  a cannula receiving chamber defined in the head and having a threaded surface;
  wherein the jaw defines opposing inner surfaces that flare outwardly with respect to each other at a location between the cannula receiving chamber and the distal end of the head, and the jaw defines opposing top and bottom surfaces, such that the inner surfaces extend between the top and bottom surfaces; wherein the cannula receiving chamber extends from the top to the bottom surfaces, and the threaded surface is fully contained between the opposing top and bottom surfaces.

16. The pair of forceps according to claim 15, wherein the head defines a tissue retracting surface having a width of at least about 15 mm.

17. The pair of forceps according to claim 15, further comprising a cannula engaged within the cannula receiving chamber, wherein the cannula includes a threaded region matable with the threaded surface of the cannula receiving chamber.

18. The pair of forceps as recited in claim 15, wherein the first and second elongated members are separable via manipulation of the first and second elongated members with respect to each other by hand without tools.

19. The pair of forceps according to claim 15, wherein the opposing inner surfaces curve away from each other from the cannula receiving chamber to the distal end of the head.

20. A pair of forceps, comprising:
  a head including a top jaw, and a bottom jaw pivotally connected to the top jaw, each of the top and bottom jaws including a head portion and an opposing handle portion that is angled with respect to the head portion at a joint;
  each of the top jaw and the bottom jaw including opposing top and bottom faces, an inner surface connected between the opposing top and bottom faces, and an outer surface opposite the inner surface and connected between the opposing top and bottom faces;
  a groove formed in each of the inner surfaces to collectively define a threaded cannula receiving chamber upon converging said top and bottom jaws, wherein the threaded cannula receiving chamber is disposed distally of the joint, and defines opposing outer terminal ends at the opposing top and bottom faces such that the chamber is fully contained between the opposing top and bottom faces, and the grooves are located at respective proximal ends so that a cannula can be positively engaged by passing the top and bottom jaws around the cannula via an engagement guide until travel is inhibited and then converging the top and bottom jaws around the cannula,
  wherein the top and bottom faces of the top and bottom jaws, respectively, extend from the joint to the threaded cannula receiving chamber, and are substantially planar from the joint to the threaded cannula receiving chamber, and the inner surfaces of the top and bottom jaw taper away from each other as the inner surfaces extend distally from the cannula receiving chamber, the tapered inner surfaces defining a gap located between the inner surfaces and distally of the cannula receiving chamber when the forceps are in a fully closed configuration.

21. The pair of forceps according to claim 20, wherein the forceps are separable without the use of tools.

22. The pair of forceps according to claim 20, wherein the head defines a tissue contacting surface that is substantially orthogonal to the inner surfaces, the tissue contacting surface has a width of at least about 15 mm.

23. The pair of forceps according to claim 20, wherein the gaps defined by the inner surfaces provide an engagement guide capable of facilitating blind location and engagement of a cannula.

24. The pair of forceps according to claim 23, wherein the engagement guide is V-shaped.

25. A pair of forceps, comprising:
  a head including a top jaw, and a bottom jaw pivotally connected to the top jaw, each of the top and bottom jaws including a head portion and an opposing handle portion that is angled with respect to the head portion at a joint;
  each of the top jaw and the bottom jaw including opposing top and bottom faces, an inner surface connected between the opposing top and bottom faces, and an outer surface opposite the inner surface and connected between the opposing top and bottom faces;
  a groove formed in each of the inner surfaces to collectively define a threaded cannula receiving chamber upon converging said top and bottom jaws, wherein the threaded cannula receiving chamber defines opposing outer terminal ends located at opposing top and bottom faces such that the chamber is fully contained between the opposing top and bottom faces, and the grooves located at the respective proximal ends so that a cannula can be positively engaged by passing the top and bottom jaws around the cannula via an engagement guide until travel is inhibited and then converging the top and bottom jaws around the cannula,
  wherein the top and bottom faces of the top and bottom jaws, respectively, extend distally from the threaded cannula receiving chamber to a terminal distal end, and are substantially planar from the cannula receiving chamber to the terminal ends; and the inner surfaces of the top and bottom jaw taper away from each other as the inner surfaces extend distally from the cannula receiving chamber, the tapered inner surfaces defining a gap located between the inner surfaces and distally of the cannula receiving chamber when the forceps are in a fully closed configuration.

26. The pair of forceps according to claim 25, wherein the top and bottom faces of the top and bottom jaws, respectively, further extend from the joint to the threaded cannula receiving chamber, and are substantially planar from the joint to the threaded cannula receiving chamber.

* * * * *